United States Patent [19]
Dancyger

[11] Patent Number: 5,267,943
[45] Date of Patent: Dec. 7, 1993

[54] WRIST AND HAND SUPPORT DEVICE

[76] Inventor: Michael Dancyger, 811 W. 58th St., Los Angeles, Calif. 90037

[21] Appl. No.: 938,944

[22] Filed: Sep. 1, 1992

[51] Int. Cl.⁵ ............................................... A61F 5/00
[52] U.S. Cl. ......................................... 602/5; 602/20; 602/21
[58] Field of Search .................. 602/5, 6, 7, 8, 12, 602/20, 21, 22, 62; 178/877, 878, 879

[56] References Cited

U.S. PATENT DOCUMENTS

| | | | |
|---|---|---|---|
| 3,238,939 | 3/1966 | Stubbs | 602/64 |
| 3,512,776 | 5/1970 | Thomas | 602/64 |
| 3,815,908 | 6/1974 | Hashimoto | 602/64 |
| 3,942,525 | 3/1976 | Dragan | 602/64 |
| 4,047,250 | 9/1977 | Norman | 602/64 |
| 4,584,993 | 4/1986 | Nelson | 602/21 |
| 4,862,877 | 9/1989 | Barber | 602/22 |

*Primary Examiner*—Michael A. Brown
*Attorney, Agent, or Firm*—Andra M. Vaccaro

[57] ABSTRACT

A flexible elastic adjustable wrist and hand support device for use by persons requiring wrist and hand support or protection is shown. The wrist support device offers generalized support to the wrist as well as lateral support to limit flexion of the wrist. The support device includes a base comprised as a flat sheet member of elastic material stretchable in a single direction circumferentially around the wrist. A plurality of longitudinal pockets are sewn into the base. Flat flexible stay members are located in the pockets to provide lateral support to the wrist. At least one flexible elastic strap is sewn onto the back of the base, such that when it surrounds the wrist of the wearer, it provides additional support and tension. The base further comprises a rigidity strap extending from said base proximate the longitudinal pockets so as to wrap around the thumb of the wearer, said strap configured in a "C"-shape on the inner side thereof and having a gently sloping edge extending from the upper edge of base which terminates in a substantially rounded edge triangular end having a first tongue-shaped member and a second narrower tongue-shaped member, which are releasably fastened to the exterior of the base, when the device is in use.

9 Claims, 4 Drawing Sheets

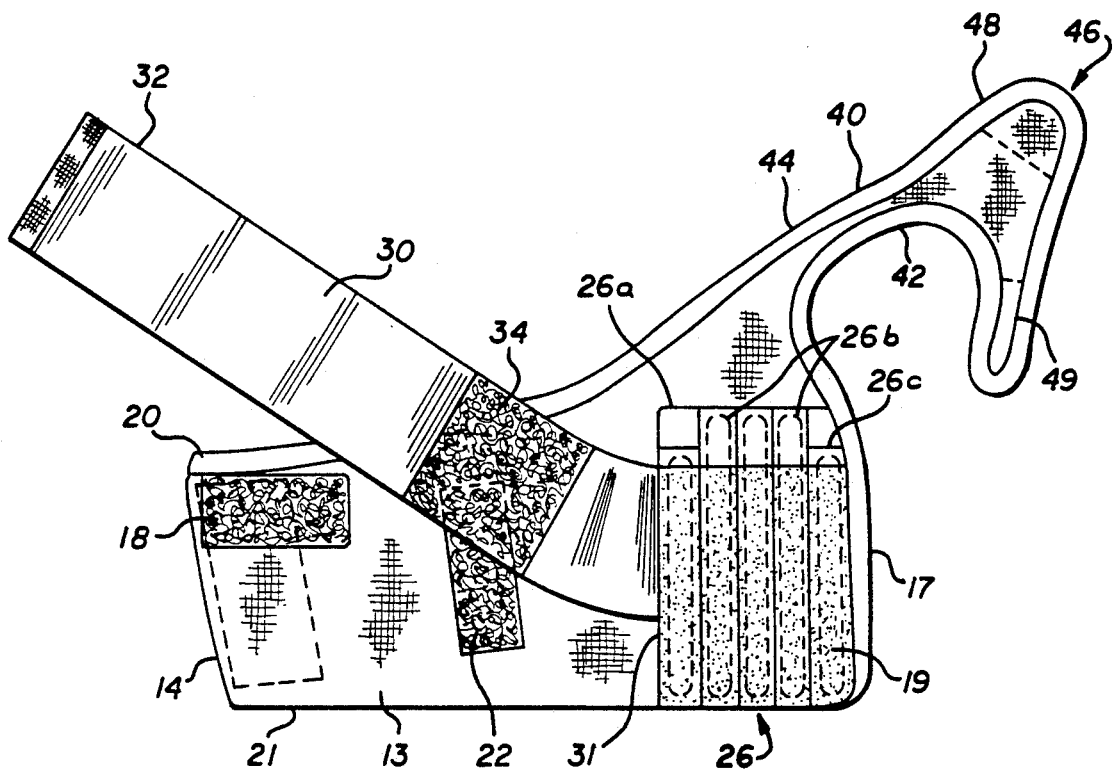

WRIST AND HAND SUPPORT DEVICE

BACKGROUND OF THE INVENTION

Field of the Invention

The invention relates to the field of orthopedic, elastic support devices for a wrist and hand, and in particular for wrist and hand supports used by construction workers, athletes and other persons who work with their hands. Its primary use is to help prevent injury and to help protect aggravation of any preexisting wrist or carpal tunnel problems.

The wrist is a complex bone and muscular structure prone to injury upon overextension or upon unusual lateral movement. Certain activities, such as hammering, drilling, computer operation, repetitive motions, bowling, etc., are particularly difficult on the wrist. In addition, the wrist may suffer a trauma, or become accidentally injured and require support. In addition, a person may have carpal tunnel syndrome requiring the person to wear a support garment on his/her wrist to secure the wrist. Surgical, rigid wrist and hand braces and casts are available, but since their goal is to immobilize the area on which they are worn, the wearer is generally unable to move his/her arm easily about. In addition, simple elastic braces are available but they have a tendency not to provide enough support to protect the wrist and hand from injury.

Other prior art wrist and hand braces are available, such as the one shown in U.S. Pat. No. 4,584,993, but they do not provide adequate support of the hand and thumb area, as does the device of the present invention, since the prior art devices merely provide support to the wrist. Further, these prior art devices, while limiting flexure of the hand and wrist in the up and down direction, do not limit the motion of the wrist from side to side, as does the device of the present invention. Additionally, the prior art devices tend to close on the upper side of the arm proximate the wrist. Since most wrist injuries tend to occur to the underside of the wrist, additional support is needed, such as provided for in the present invention. Further, they are not as adaptable to any hand size or shape or use as does the device of the present invention.

SUMMARY OF INVENTION

The present invention relates to a flexible elastic wrist support device for use by construction workers and other persons requiring wrist and hand support. The wrist and hand support device offers lateral support to the wrist to limit the flexure and hyperextension of the wrist. The wrist and hand support device includes a base comprised as a flat sheet member of elastic material stretchable in a single direction circumferentially around the wrist so as to form a form fitting sleeve around the wrist of the user. A plurality of spaced apart longitudinal pockets are sewn onto the middle area of the base in a direction perpendicular to the circumference thereof. Flat flexible stay members are enclosed in the pockets to provide firm lateral support to the under side of the wrist. Each end of outer portion of the base is comprised of hook and loop closure or other suitable attachment means. On the underside of one end of the base is the reciprocal area of hook and loop closure or other suitable attachment means so that the base can be fixedly enclosed around the wrist of the user.

A specially configured rigidity strap extends from the base proximate the longitudinal pockets, to wrap around the thumb allowing freedom of motion for the thumb. The rigidity strap is pulled around the thumb, over the back of the hand and is releasably fastened to the back of the base proximate the back of the hand and also fastened to the base proximate the underside of the hand. This rigidity strap fixes the position of the support device on the wearer and offers support to both the hand pad and the wrist such that the motion of the wrist is limited from side to side as well as up and down motion.

One or more additional releasable flexible elastic straps comprised of a flat sheet stretchable in a single direction circumferentially around the wrist may also be affixed to the back of the base for adding additional tension to the base support. The support device is adjustable to fit varying sizes of wrists. The elastic straps provide additional tension to the base support.

BRIEF DESCRIPTION OF THE DRAWINGS

FIG. 4 is a plan view of the exterior of the preferred embodiment of the wrist and hand support device in unwrapped condition;

FIG. 5 is an elevational view of the preferred embodiment of the wrist and hand support device in a partially installed condition;

DESCRIPTION OF PREFERRED EMBODIMENTS

Figure 1:
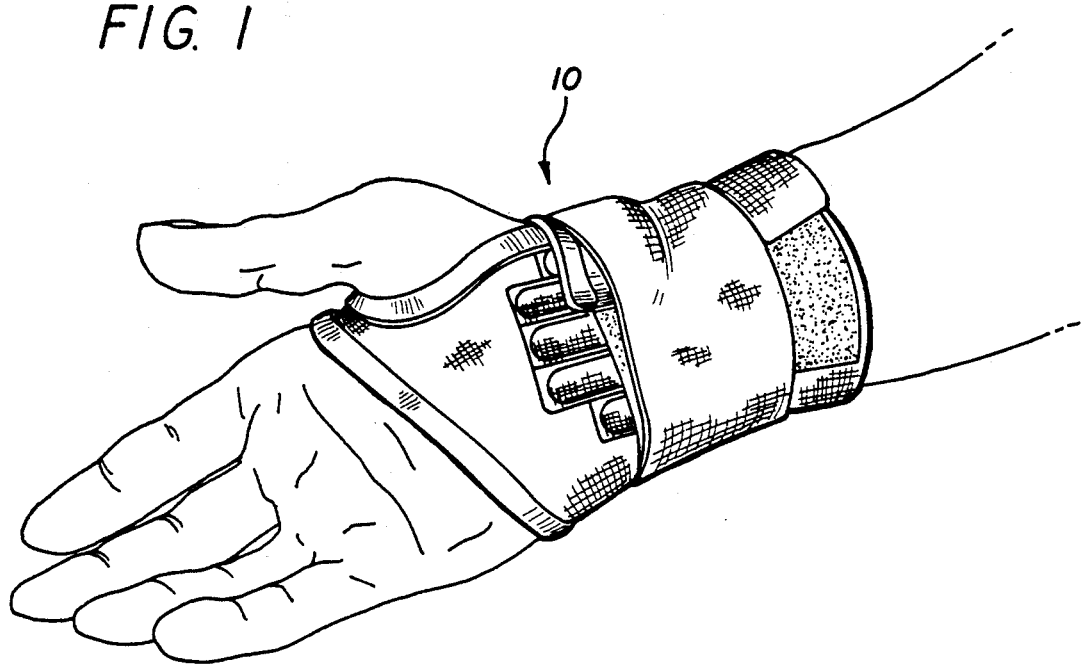
FIG. 1 is a perspective view of the front of the underside of the preferred embodiment of the wrist and hand support device as worn by a user of the device.
Figure 2:
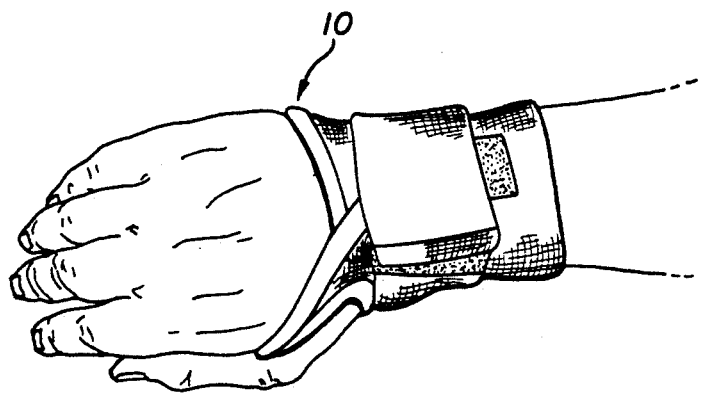
FIG. 2 is a perspective view of the top side of the preferred embodiment of the wrist and hand support device as worn by a user of the device.

Referring first to the drawings, there is shown in FIGS. 1 through 5 a wrist and hand support device 10 having a flat base 12. Base 12 is preferably formed of a substantially rigid, linearly elastic fabric, capable of being stretched circumferentially around the wrist of the wearer. Base 12 has an exterior side 13 and an interior side 15 and a proximate and a distal end 14 and 17, respectively. Affixed proximate the distal end 17 of the base 12 is a fastening means 19.

Figure 3:
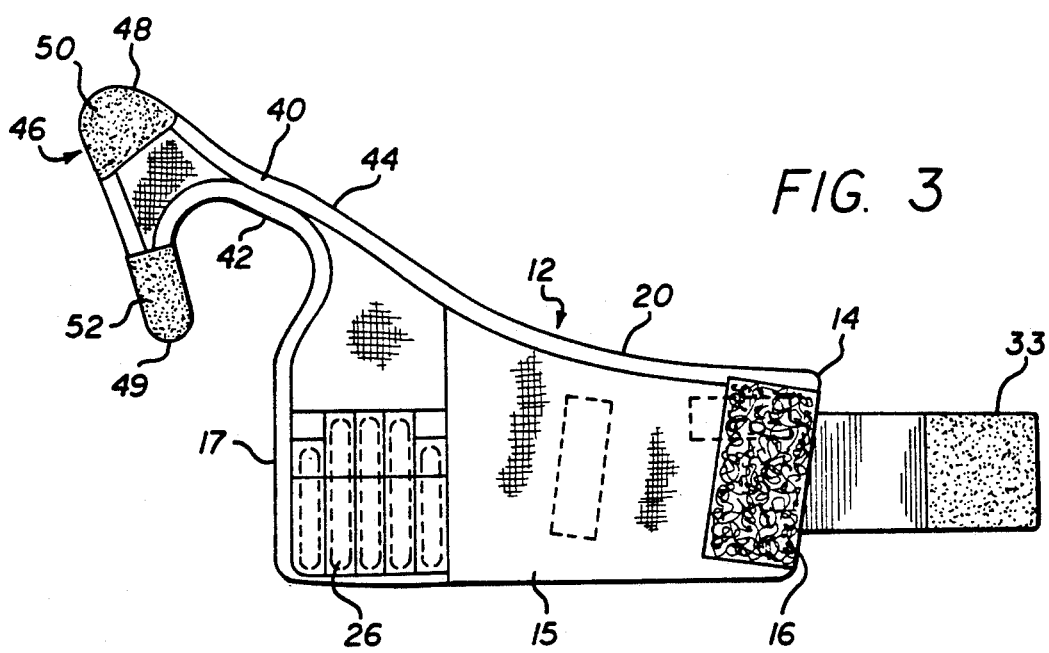
FIG. 3 is a plan view of the interior of the preferred embodiment of the wrist and hand support device in an unwrapped condition.

As shown more clearly in FIG. 3, affixed to the interior 15 of the base proximate and extending substantially along its distal end 14 is a first fastening means 16. The fastening mean 16 is fastened along the first end 14 of the interior 15 of base 12 by suitable means such as sewing. Additional fastening means 50, and 52 are also fastened to the interior 15 of base 12 proximate distal end 17.

Referring more specifically to FIG. 4, a second fastening means 18 is attached to the exterior 13 of base 12 proximate its distal end 17. Fastening means 18 is attached to base 12, by suitable means such as sewing, so that it is proximate and parallel to its upper lateral edge 20. A third fastening means 22 is also attached to the exterior 13 of base 12 so that it is approximately midway between and parallel to proximate and distal ends 14 and 17, respectively.

Referring specifically to FIGS. 1, 3 and 4, a plurality of elongated, parallel longitudinal pockets 26 are affixed next to the proximate end 17 of the exterior 13 of the base 12. The pockets 26 extend perpendicularly to the bottom edge 21 of base 12. An elongated flexible supporting stay member (not shown) is fixedly located in each of the pockets 26. In the preferred embodiment, the outer pockets 26a and 26c contain stays that are shorter than the interior pockets 26b. Each stay member is comprised as a resilient flat stay member that cannot be compressed longitudinally. The stay members provide resistance against flexure of the wrist when the wrist support device is properly fixed in place and also prevents overextension and hyperextension of the wrist muscles and joints. In the preferred embodiment, there are 5–9 stays and the material enclosing the stays provides padding.

An elongated elastic support strap 30 (see FIGS. 3, 4 and 5) is formed of a linearly elastic fabric preferably stretchable circumferentially around the wrist of the wearer. Strap 30 is affixed proximate the center 31 of pocket 26c on the exterior 13 of base 12. In the preferred embodiment, the strap 30 is affixed so that it is centered between and parallel to the lateral edges 20 and 21 of base 12. The strap 30 has an end 32 which is extendable around the wrist with base 12 in place on the wrist to offer the appropriate tension of the device around the wrist. Coextensive with the lateral edge of the interior of end 32 of strap 30 is fastening strip 33. A second fastening means 34 is fastened along the exterior of strap 30, such that it is located substantially above fastening means 22 on base 12. The amount of tension is adjustable according to where fastening strip 33 is affixed onto fastening strip 34 on the exterior of strap 30 as it is wrapped around the wrist of the wearer. (See FIGS. 1 through 5.)

Referring specifically to FIGS. 3 and 4, a specially configured rigidity strap 40 extends from the base 12 proximate the longitudinal pockets 26, to wrap around the thumb (see FIG. 5) allowing freedom of motion for the thumb. The strap 40 is configured in a "C"-shape on the inner side 42 and has a gently sloping edge 44 extending from the upper lateral edge 20 of base 12. The strap 40 terminates in a substantially rounded edge triangular end 46 having a first tongue-shaped member 48 and a second narrower tongue-shaped member 49. Along the interior of end 46, at the tip of tongue-shaped members 48 and 49 are fastening means 50 and 52, respectively. Strap 40 is substantially narrow around the center of the "C" shape in order to comfortably fit around the thumb, between the thumb and the forefinger.

The base 12 is capable of surrounding the wrist so as to form a sleeve by fastening the ends of base 12 together.

Use of the wrist supporting device 10 is illustrated in FIGS. 1, 2, 5 and 6. The wrist support is used by placing the interior 15 of base 12 to which stays 26 are fastened, against the portion of the arm proximate the wrist. Free end 14 of base 12 is wrapped around the wrist of the user such that fastening means 16 is overlapped and fastened onto end 17 by releasably fastening strips 16 and 19 to each other to releasably hold base 12 in tension. The rigidity strap 40 is then pulled around the thumb, over the back of the hand and fastening means 50 is releasably fastened to fastening means 22 on the back of the base and fastening means 52 is releasably fastened to fastening means 18 on the back of the base. Due to the fact that the rigidity strap 40 is fastened to the base at two locations rather than one as in prior art devices, there is greater support of the hand pad and wrist and it is less likely to come off the hand during use. The rigidity strap also fixes the position of the brace around the wrist of the wearer.

The wearer then pulls the elongated elastic support strap 30 (see FIGS. 3, 4 and 5) circumferentially around the wrist of the wearer such that fastening means 33 is attached to fastening means 34. The mount of tension is adjustable according to where fastening strip 33 is affixed onto fastening strip 34 on the exterior of strap 30 as it is wrapped around the wrist of the wearer. (See FIGS. 1 through 5.)

Figure 6:
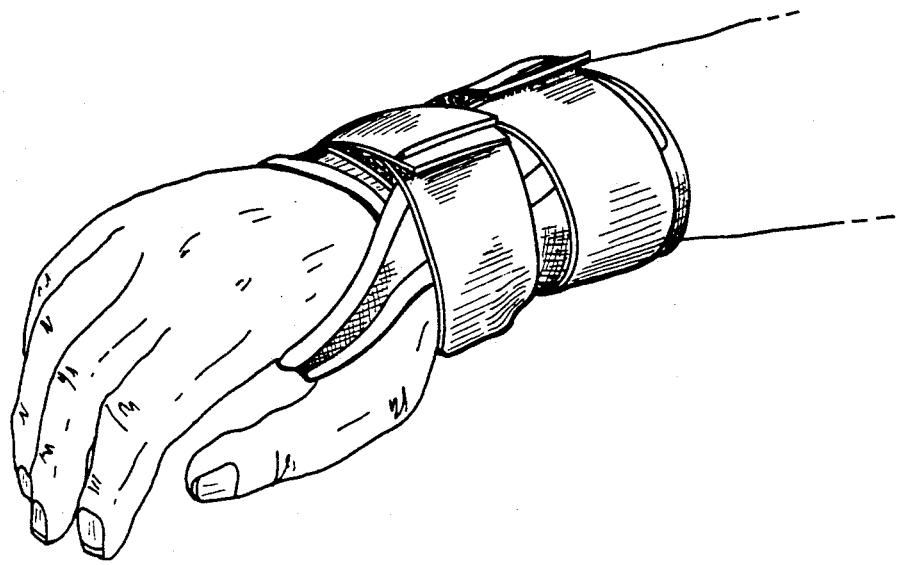
FIG. 6 is a perspective view of the top side of an alternate embodiment of the wrist and hand support device as worn by a user of the device.
Figure 7:
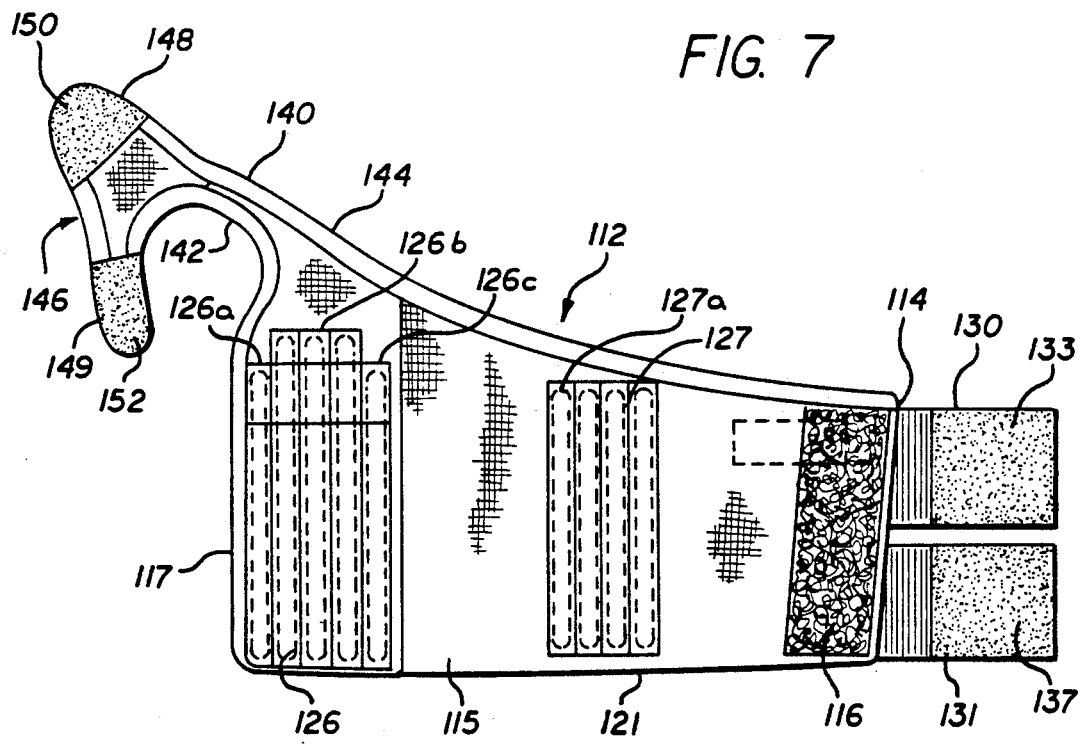
FIG. 7 is a plan view of the interior of an alternate embodiment of the wrist and hand support device in an unwrapped condition.
Figure 8:
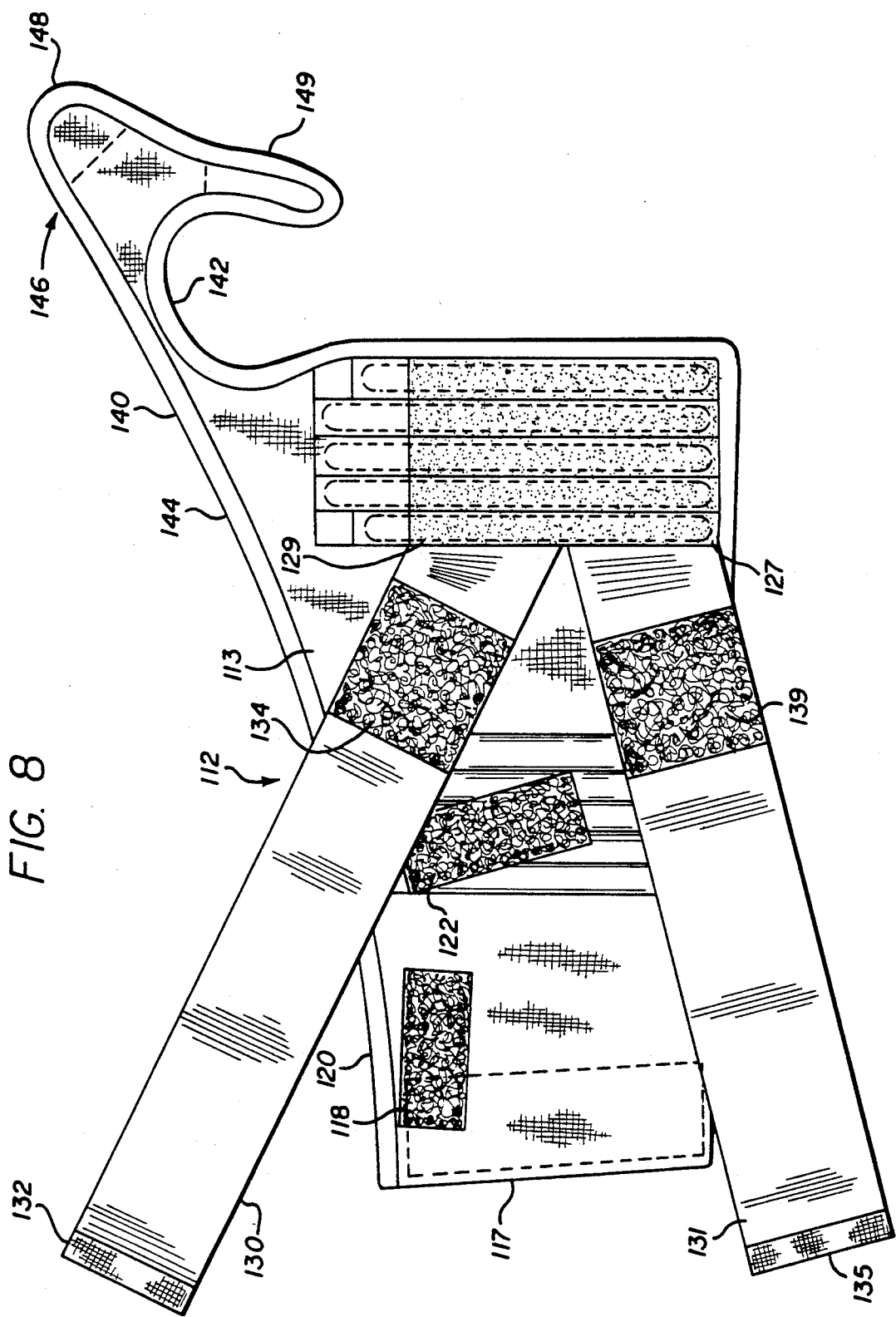
FIG. 8 is a plan view of the exterior of an alternate embodiment of the wrist and hand support device in unwrapped condition.

Referring next to FIGS. 6, 7 and 8, an alternate embodiment of the present invention is shown. A base 112 is shown, which is identical in shape and size to base 12 shown in FIGS. 1-5. Base 112 is preferably formed of a substantially rigid, linearly elastic fabric, capable of being stretched circumferentially around the wrist of the wearer. Base 112 has an exterior side 113 and an interior side 115 and a proximate and a distal end 114 and 117, respectively.

As shown more clearly in FIG. 7, affixed to the interior 115 of the base proximate and extending substantially along its distal end 114 is a first fastening means 116. The fastening mean 116 is fastened along the first end 114 of the interior 115 of base 112 by suitable means such as sewing. Additional fastening means 150, and 152 are also fastened to the interior 115 of base 112 proximate distal end 117.

Referring more specifically to FIG. 8, a second fastening means 118 is attached to the exterior 113 of base 112 proximate its distal end 117. Fastening means 118 is attached to base 112, by suitable means such as sewing, so that it is proximate and parallel to its upper lateral edge 120. A third fastening means 122 is also attached to the exterior 113 of base 112 so that it is approximately midway between and proximate and distal ends 114 and 117, respectively and vertical to the lateral edge 120 of the device.

Referring specifically to FIGS. 6, 7 and 8, a first set of a plurality of elongated, parallel longitudinal pockets 126 are affixed next to the distal end 117 of the exterior 113 of the base 112. The pockets 126 extend perpendicularly to the bottom edge 121 of base 112. A second set of a plurality of elongated, parallel longitudinal pockets 127 are affixed to the base 112 under the fastening means 122 so that they are approximately half way between the distal and proximate ends 114 and 117 of the base 112. The pockets 127 extend perpendicularly to the bottom edge 121 of base 112. An elongated flexible supporting stay member (not shown) is fixedly located in each of the pockets 126 and 127. In the preferred embodiment, the outer pockets 126a and 126c contain stays that are shorter than the interior pockets 126b. Likewise the pockets 127a contain stays that are the approximate size of stays 126a and 126c. Each stay member is comprised as a resilient flat stay member that cannot be compressed longitudinally. The stay members provide resistance against flexure of the wrist when the wrist and hand support device is properly fixed in place and also prevents overextension and hyperextension of the wrist muscles and joints. In the preferred embodiment, there are 5-9 stays and the material enclosing the stays provides padding.

Elongated elastic support straps 130 and 131 (see FIGS. 6, 7 and 8) are formed of a linearly elastic fabric preferably stretchable circumferentially around the wrist of the wearer. Strap 130 is affixed proximate the upper portion 129 of pocket 126c on the exterior 113 of base 112. Strap 131 is affixed proximate the lower portion 127 of pocket 126c on the exterior 113 of base 112. In the preferred embodiment, straps 130 and 131 are affixed so that they are centered between and parallel to the lateral edges 120 and 121 of base 112. Straps 130 and 131 have ends 132 and 135, respectively, which are extendable around the wrist with base 112 in place on the wrist to offer the appropriate tension of the device around the wrist. Coextensive with each of the lateral edges of the interior of end 132 of strap 130 and the interior of 135 of strap 131 are fastening strips 133 and 137, respectively. Fastening means 134 and 139 are fastened along the exteriors of straps 130 and 131, respectively, such that they are located substantially above fastening means 122 on base 112. The amount of tension is adjustable according to where fastening strips 133 and 137 are affixed onto fastening strips 134 and 139, respectively, on the exterior of straps 130 and 131, respectively, as they are wrapped around the wrist of the wearer. (See FIGS. 6 through 8.)

Referring specifically to FIGS. 7 and 8, a specially configured rigidity strap 140 extends from the base 112 proximate the longitudinal pockets 126, to wrap around the thumb (see FIG. 5) allowing freedom of motion for the thumb. The strap 140 is configured in a "C"-shape on the inner side 142 and has a gently sloping edge 144 extending from the upper lateral edge 120 of base 112. The strap 140 terminates in a Substantially rounded edge triangular end 146 having a first tongue-shaped member 148 and a second narrower tongue-shaped member 149. Along the interior of end 146, at the tip of tongue-shaped members 148 and 149 are fastening means 150 and 152, respectively. Strap 140 is substantially narrow around the center of the "C" shape in order to comfortably fit around the thumb, between the thumb and the forefinger.

In use, the rigidity strap 140 is pulled around the thumb, over the back of the hand and fastening means 150 is releasably fastened to fastening means 122 on the back of the base and fastening means 152 is releasably fastened to fastening means 118 on the back of the base. Due to the fact that the rigidity strap 140 is fastened to the base at two locations rather than one as in prior art devices, there is greater support of the hand pad and wrist and it is less likely to come off the hand during use. The rigidity strap also fixes the position of the brace around the wrist of the wearer.

Use of the alternate embodiment of the wrist and hand supporting device is illustrated in FIGS. 6-8. The wrist and hand support is used by placing the interior 115 of base 112 to which stays 126 are fastened, against the portion of the arm proximate the wrist. Free end 114 of base 112 is wrapped around the wrist of the user such that fastening means 116 is overlapped and fastened onto end 117 by releasably fastening strips 116 and 117 to each other to releasably hold base 112 in tension. The base 112 is placed such that stays 127 are resting against the upper side of the wrist for additional support. The rigidity strap 140 is then pulled around the thumb, over the back of the hand and fastening means 150 is releasably fastened to fastening means 122 on the back of the base and fastening means 152 is releasably fastened to fastening means 118 on the back of the base. Due to the fact that the rigidity strap 140 is fastened to the base at two locations rather than one as in prior art devices, there is greater support of the hand pad and wrist and it is less likely to come off the hand during use. The rigidity strap also fixes the position of the brace around the wrist of the wearer.

The wearer then pulls the elongated elastic support straps 130 and 131 (see FIGS. 6, 7 and 8) Circumferentially around the wrist of the wearer such that fastening means 133 and 137 are attached to fastening means 134 and 139, respectively. The amount of tension is adjustable according to where fastening strips 133 and 137 are affixed onto fastening strips 134 and 139, respectively, on the exterior of straps 130 and 131, respectively, as they are wrapped around the wrist of the wearer. (See FIGS. 6 through 8.)

The fastening means referred to herein are formed of materials that releasable adhere to each other when pressed together such as Velcro.

The devices of the present invention provides much more support to the wrist and hand than does prior art devices. For example, the device disclosed in U.S. Pat. No. 4,584,993 provides a top closure, while the devices of the present invention provide a bottom closure, and thus an overlap of material on the bottom of the wrist. This provides additional support and rigidity to the wrist proximate the location where most wrist accidents occur. In the second embodiment of the invention, even more support is given due to the additional set of stays placed in the device proximate the wrist and hand area.

In the devices of the present invention, the stays are shorter proximate the outsides of the palm of the hand, so as to conform to the contour of the hand, therefore providing more and more comfortable support in the area where carpal tunnel syndrome occurs most, i.e. in the center of the hand and up the center of the wrist.

In addition, all the binding of the edges of the devices of the present invention are elastic in order to provide maximum support of the wrist. The rigidity straps 40 and 140 are shaped so as to support the wrist during lateral movement i.e. from side to side, in addition to the up and down motion of the prior art devices.

While particular embodiments of the invention have been shown and illustrated herein, it will be understood that many changes, substitutions and modifications may be made by those persons skilled in the art, such as, by way of example and not limitation, additional stays, straps, etc. The configurations may be reversed to accommodate left handed, as well as, right handed wearers. It will be appreciated from the above description of presently preferred embodiments that other configurations are possible and within the scope of the present invention. Thus, the present invention is not intended to be limited to the particular embodiments specifically discussed hereinabove.

What is claimed is:

1. A wrist and hand support device comprising:
   a generally flat base having an interior and an exterior side, a top edge and a bottom edge, comprising elastic material stretchable in at least one direction circumferentially around a user's wrist, said base having a proximate and a distal end;
   first fastening means attached to the interior of said base proximate the proximate end;

second fastening means attached to said exterior of said base proximate the distal end;

third fastening means attached to the exterior of said base along the upper edge thereof, proximate the proximate end;

fourth fastening means attached to the exterior of said base between said proximate and said distal ends;

a first plurality of spaced apart longitudinal pockets sewn onto said base in a direction perpendicular to the circumference thereof proximate the distal end;

flat flexible stay members enclosed in each of said pockets;

a first flexible elastic strap affixed to said base proximate said pockets on the exterior of said base, said strap being located substantially between and parallel to the edges of said base having a first end and a interior and exterior side, said strap comprised of a flat sheet of elastic material stretchable in at least one direction circumferentially around the wrist;

fifth fastening means coextensive with the lateral edge of the interior of the end of said strap;

sixth fastening means fastened along the exterior of said strap, such that it is located substantially above said second fastening means on said base, such that the tension of said strap is adjustable according to where said fifth fastening means is affixed onto sixth fastening means as it is wrapped around the wrist of the wearer;

rigidity strap means extending from said base proximate the longitudinal pockets so as to wrap around the thumb of the wearer, said strap configured in a C-shape on the inner side thereof and having a gently sloping edge extending from the upper edge of base which terminates in a substantially rounded edge triangular end having a first tongue-shaped member and a second narrower tongue-shaped member;

seventh and eighth fastening means attached to the interior of said triangular end, at the tip of said first and said second tongue-shaped member, respectively;

whereby, in use, the interior of said base where said stays are fastened are placed against the portion of the arm proximate the wrist, then the distal end of said base is wrapped around the wrist of the user such that said first fastening means is releasably fastened to said second fastening means to hold said base in tension, said rigidity strap means being pulled around the thumb, over the back of the hand and said seventh and eighth fastening means being releasably fastened to third and fourth fastening means respectively; said elastic support strap being placed circumferentially around the wrist of the wearer such that fifth fastening means is attached to said sixth fastening means, such that the wrist of the wearer is supported.

2. The wrist and hand support device of claim 1 wherein said fastening means comprise hook and loop means.

3. The wrist and hand support of claim 1 wherein said flexible elastic strap comprises linearly elastic fabric preferable stretchable circumferentially around the wrist of the wearer, which is affixed proximate to the center of the outer portion of the base adjacent to the center of said longitudinal pockets.

4. The wrist and hand support of claim 1 further comprising:

a second plurality of spaced apart longitudinal pockets sewn onto said base in a direction perpendicular to the circumference thereof located between the distal and proximate ends such that when the device is worn, the second set of pockets is located over the top of the wrist of the wearer; and flat flexible stay members enclosed in each of said pockets.

5. The wrist and hand support of claim 1 further comprising a second flexible elastic strap affixed to said base proximate said pockets on the exterior of said base and adjacent to said first flexible elastic strap, having a first end and a interior and exterior side, said strap comprised of a flat sheet of elastic material stretchable in at least one direction circumferentially around the wrist;

ninth fastening means coextensive with the lateral edge of the interior of the end of said second strap;

tenth fastening means fastened along the exterior of said second strap, such that it is located substantially above said second fastening means on said base, such that the tension of said second strap is adjustable according to where said ninth fastening means is affixed onto said tenth fastening means as it is wrapped around the wrist of the wearer.

6. The wrist and hand support of claim 1 wherein said flat flexible stay members cannot be compressed longitudinally in order to provide support and limit flexure of the wrist.

7. A wrist and hand support device comprising:

a generally flat base having an interior and an exterior side, a top edge and a bottom edge, comprising elastic material stretchable in at least one direction circumferentially around a user's wrist, said base having a proximate and a distal end;

first fastening means attached to the interior of said base proximate the proximate end;

second fastening means attached to said exterior of said base proximate the distal end;

third fastening means attached to the exterior of said base along the upper edge thereof, proximate the proximate end;

fourth fastening means attached to the exterior of said base between said proximate and said distal ends;

a first plurality of spaced apart longitudinal pockets sewn onto said base in a direction perpendicular to the circumference thereof proximate the proximate end;

a second plurality of spaced apart longitudinal pockets sewn onto said base in a direction perpendicular to the circumference thereof located between the distal and proximate ends such that when the device is worn, the second set of pockets is located over the top of the wrist of the wearer; and flat flexible stay members enclosed in each of said pockets;

a first flexible elastic strap affixed to said base proximate said pockets on the exterior of said base, said strap being located substantially between and parallel to the edges of said base having a first end and a interior and exterior side, said strap comprised of a flat sheet of elastic material stretchable in at least one direction circumferentially around the wrist;

fifth fastening means coextensive with the lateral edge of the interior of the end of said strap;

sixth fastening means fastened along the exterior of said strap, such that it is located substantially above said second fastening means on said base, such that the tension of said strap is adjustable according to where said fifth fastening means is affixed onto sixth fastening means as it is wrapped around the wrist of the wearer;

rigidity strap means extending from said base proximate the longitudinal pockets so as to wrap around the thumb of the wearer, said strap configured in a C-shape on the inner side thereof and having a gently sloping edge extending from the upper edge of base which terminates in a substantially rounded edge triangular end having a first tongue-shaped member and a second narrower tongue-shaped member;

seventh and eighth fastening means attached to the interior of said triangular end, at the tip of said first and said second tongue-shaped member, respectively;

whereby, in use, the interior of said base where said stays are fastened are placed against the portion of the arm proximate the wrist, then the distal end of said base is wrapped around the wrist of the user such that said first fastening means is releasably fastened to said second fastening means to hold said base in tension, said rigidity strap means being pulled around the thumb, over the back of the hand and said seventh and eighth fastening means being releasably fastened to third and fourth fastening means respectively; said elastic support strap being placed circumferentially around the wrist of the wearer such that fifth fastening means is attached to said sixth fastening means, such that the wrist of the wearer is supported.

8. The wrist and hand support of claim 7 further comprising a second flexible elastic strap affixed to said base proximate said pockets on the exterior of said base and adjacent to said first flexible elastic strap, having a first end and a interior and exterior side, said strap comprised of a flat sheet of elastic material stretchable in at least one direction circumferentially around the wrist;

ninth fastening means coextensive with the lateral edge of the interior of the end of said second strap;

tenth fastening means fastened along the exterior of said second strap, such that it is located substantially above said second fastening means on said base, such that the tension of said second strap is adjustable according to where said ninth fastening means is affixed onto said tenth fastening means as it is wrapped around the wrist of the wearer.

9. The wrist and hand support of claim 7 wherein said flat flexible stay members cannot be compressed longitudinally in order to provide support and limit flexure of the wrist.

* * * * *